United States Patent [19]

Katsumata et al.

[11] Patent Number: 4,560,661

[45] Date of Patent: Dec. 24, 1985

[54] PROCESS FOR PURIFYING ENZYMES

[75] Inventors: Hideo Katsumata, Gotenba; Shigeo Katsumata, Mishima; Shinzo Ishii, Shizuoka; Yuko Arai, Susono, all of Japan

[73] Assignee: Kyowa Hakko Kogyo Co., Ltd., Tokyo, Japan

[21] Appl. No.: 488,174

[22] Filed: Apr. 25, 1983

[30] Foreign Application Priority Data

Apr. 27, 1982 [JP] Japan .................................. 57-70598

[51] Int. Cl.[4] .......................... C12N 9/00; C12N 9/02; C12N 9/04; C12N 9/14; C12N 9/20; C12N 9/88; C12N 9/90; C12N 9/92

[52] U.S. Cl. .................................... 435/183; 435/189; 435/190; 435/195; 435/198; 435/232; 435/233; 435/234; 435/815

[58] Field of Search ................. 435/815, 183, 189–234

[56] References Cited

U.S. PATENT DOCUMENTS 2,952,586  9/1960  Okunuki et al. ................. 435/815 X

FOREIGN PATENT DOCUMENTS 2082188  3/1982  United Kingdom .

OTHER PUBLICATIONS

Journal of Fermentation Technology, vol. 58, No. 5, pp. 423–429, (1980).
Chemical Abstract vol. 93:234004b, (1980).
Chemical Abstract vol. 97:68552q, (1984).

*Primary Examiner*—Lionel M. Shapiro
*Attorney, Agent, or Firm*—Fitzpatrick, Cella, Harper & Scinto

[57] ABSTRACT

Disclosed is a process for purifying an enzyme contained in a solution such as cell extract liquor or fermentation culture liquor. The crude enzyme solution is brought into contact with either a strongly acidic cation exchange resin of high porous type or a strongly basic anion exchange resin of high porous type to adsorb the enzyme on the resin. An eluting agent is then passed through the resin to elute out the enzyme as a purified enzyme solution.

5 Claims, No Drawings

PROCESS FOR PURIFYING ENZYMES

BACKGROUND OF THE INVENTION

The present invention pertains generally to a process for purifying an enzyme and, more specifically, an improved process for obtaining a purified enzyme solution from a crude enzyme containing solution such as a cell extract liquor, a fermentation culture liquid or the like.

Heretofore, various processes have been employed for purifying enzymes, and processes using synthetic adsorbents, weakly basic anion exchange resins, weakly acidic cation exchange resins, and adsorbents such as cellulose, Sephadex, carbon, etc. are known. However, these processes suffer from various drawbacks which render them unsuitable for enzyme purification on a commercial scale. That is, in many processes using a synthetic adsorbent such as resins of the Amberlite XAD series (trademark for products of Rohm and Haas Co.), resins of the Diaion HP series (trademark for products of Mitsubishi Kasei Kogyo Co.), etc., the enzyme is either poorly adsorbed onto the resins by contact of an enzyme solution with the resins or, if adsorbed, is hardly eluted by an eluting agent. Moreover, the species of enzyme to which these processes are applicable are limited to protease, amylase, etc.

The processes using Sephadex having ion exchange groups are excellent in chromatographic separation, but a high flow rate cannot be obtained in column operation, and, thus, are not applicable to a commercial scale process. Ion exchange resins in the nature of weakly acidic cation exchange resin such as Amberlite IRC-50 and CG-50 (trademarks for products of Rohm and Haas Co.), weakly basic anion exchange resin such as Duolite A-7 (trademark for product of Diamond Shamrock Co.), etc. are known. However, since these ion exchange resins do not have the ability to decompose neutral salts and have a small specific surface area, they also have serious drawbacks. For example, the enzyme cannot be adsorbed onto the ion exchange resins or only a very small amount of enzyme can be adsorbed from a crude enzyme solution containing a large amount of impurities, or from a solution wherein the enzyme is dissolved in a solution of salts of high ionic intensity, a buffer solution, etc. Thus, these ion exchange resins are also not practical.

It has been proposed that strongly acidic cation exchange resins of macroreticular structure type such as AGMP-50 (trademark for a product of Bio. Rad Laboratory Co.) are applicable for adsorption and elution of an enzyme, but the adsorption rate is not specified and it is not certain that these resins are practically applicable.

On the other hand, it is known to use strongly basic anion exchange resins such as Amberlite IRA-904 and IRA-938 (trademarks for products of Rohm and Haas Co.) of macroreticular structure type in adsorption and elution of pepsin and analysis of creatinine kinase.

Therefore, a need exists for an improved process for purification of a crude enzyme solution which is applicable to a commercial scale. To this end, it has now been found that when various enzyme solutions are brought into contact with a strongly acidic cation exchange resin of high porous type or a strongly basic anion exchange resin of high porous type, the enzyme is adsorbed onto the ion exchange resin at a high adsorption rate, i.e. in a high adsorption amount, and when the resin is eluted with an appropriate eluting agent, the enzyme can be desorbed into the eluate in a high yield with a considerable increase in specific enzyme activity.

SUMMARY OF THE INVENTION

In accordance with the present invention, an enzyme is purified from a crude enzyme solution by a process which comprises bringing said solution into contact with a strongly acidic cation exchange resin of high porous type or a strongly basic anion exchange resin of high porous type whereby said enzyme is adsorbed on said resin; passing an eluting agent through said resin to elute said enzyme therefrom; and thereafter recovering active fractions containing said enzyme. If necessary, impurities may be removed from the ion exchange resin by washing with water prior to the elution step.

The strongly basic anion exchange resin of high porous type to be used in the present invention, which belongs to the resins of macroreticular structure type, provides twice or more higher enzyme adsorption rate and 1-3 times greater increase of a specific enzyme activity as compared with the strongly basic anion exchange resins of macroreticular structure type, such as Amberlite IRA-904 and IRA-938 which are known to be applicable for adsorption and elution of certain enzymes. On the other hand, the strongly acidic cation exchange resin of high porous type to be used in the present invention, which belongs to the resins of macroreticular structure type, provides twice to three times emzyme adsorption rate as compared with the strongly acidic cation exchange resins of macroreticular structure type such as AGMP-50 and Duolite C-10 (trademark of product made by Diamond Shamrock Co.), which are said to be applicable for adsorption and elution of an enzyme. Accordingly, the present invention provides a very practical process for purifying an enzyme on an industrial scale.

DESCRIPTION OF THE INVENTION

The ion exchange resin of macroreticular structure to be used in the present invention can be exemplified by ion exchange resins having a structure wherein a quaternary ammonium group or a sulfo group is introduced as exchange groups into a styrene-divinylbenzene polymer matrix of macroreticular structure. For example, Diaion HPA-25 and HPA-75 (trademarks for products of Mitsubishi Kasei Kogyo Co.), are illustrative of the strongly basic anion exchange resin of high porous type. Diaion HPK-16, HPK-25, HPK-30, HPK-40 (trademarks for products of Mitsubishi Kasei Kogyo Co.), are illustrative of the strongly acidic cation exchange resin of high porous type.

As shown in Table 1, these ion exchange resins have a large average pore radius of 150 Å or more, a large specific surface area of 5 $m^2/g$ dry resin or more, and a large pore volume of 0.2 $cm^3/g$ dry resin or more. Therefore, a considerable amount of the enzyme molecules can pass into or out of the macropores even if they have a high molecular weight, which is presently believed to be the reason for the high adsorption rate and high elution rate of these resins.

TABLE 1
Physical Properties of Ion Exchange Resins

| Resin (trademark) | Type | Exchange capacity meq/ml resin | Average pore radius (Å) | Specific surface area (m²/g) | Pore volume (cm³/g) |
|---|---|---|---|---|---|
| Diaion HPA25 | high porous | 0.58 | 500~800 | 33.8 | 0.97 |
| Diaion HPA75 | high porous | 0.49 | 500~600 | 30.5 | 0.88 |
| Diaion HPK16 | high porous | ≧1.7 | 623 | 5 | 0.22 |
| Diaion HPK25 | high porous | ≧1.8 | 280 | 12.7 | 0.26 |
| Diaion HPK30 | high porous | ≧1.7 | 226 | 21.8 | 0.29 |
| Diaion HPK40 | high porous | ≧1.3 | 190 | 52.2 | 0.40 |

Since the exchange groups of ion exchange resins to be used in the present invention are strongly basic or strongly acidic, the resins show a strong ion exchange action. Therefore, even if the resins are brought into contact with enzymes existing in a solution containing salts at high concentration, a buffer solution at high concentration or a solution containing a large amount of impurities, the resins can adsorb the enzymes.

Adsorption and elution tests with various enzymes have been carried out and the adsorption rates and elution rates thus obtained are set forth in the following Table 2. As will be apparent from the data in Table 2, a very wide range of enzymes are effectively purified by the process of the present invention.

| Resin | Enzyme | Enzyme-producing strain, accession number | Adsorption rate | Elution rate | Specific activity elevation[*1] |
|---|---|---|---|---|---|
| Diaion HPA-25 | Lipoprotein lipase | Rhizopus japonicus FERM P-3651 | 60.6 IU/ml[*2] | 63.3% | 11 |
| Diaion HPA-75 | Lipoprotein lipase | Rhizopus japonicus FERM P-3651 | 93.6 | 51.2 | 15 |
| Amberlite IRA-904 | Lipoprotein lipase | Rhizopus japonicus FERM P-3651 | 54.3 | 20.8 | 5 |
| Amberlite IRA-938 | Lipoprotein lipase | Rhizopus japonicus FERM P-3651 | 16.7 | 50.9 | 7 |
| Dowex IX8 | Lipoprotein lipase | Rhizopus japonicus FERM P-3651 | 0 | 0 | — |
| Duolite A-7 | Lipoprotein lipase | Rhizopus japonicus FERM P-3651 | 5 | 20 | 3 |
| Diaion HPA-25 | Pyranose oxidase | Coriolus versicolor ATCC 20155 | 2 | 77 | 17.8 |
| Diaion HPA-25 | Protease | Streptomyces scabies ATCC 15485 | 4000 | 80 | 15.5 |
| Diaion HPA-25 | Malate dehydrogenase | Alcaligenes faecalis ATCC 8750 | 700 | 91.5 | 5.0 |
| Diaion HPA-25 | Lactate dehydrogenase | Lactobacillus bulgaricus IAM 1120 | 400 | 87.5 | 15.0 |
| Diaion HP-20 | Protease | Streptomyces scabies ATCC 15485 | 4000 | 30 | 5 |
| Diaion HPK-25 | Glutaminase | Pseudomonas sp. P-210 ATCC 21025 | 80 | 70 | 40.0 |
| Diaion HPK-30 | " | Pseudomonas sp. P-210 ATCC 21025 | 80 | 65 | 42.0 |
| Diaion HPK-40 | " | Pseudomonas sp. P-210 ATCC 21025 | 55 | 65 | 40.0 |
| Amberlite 200C | " | Pseudomonas sp. P-210 ATCC 21025 | 25 | 70 | 30 |
| Dowex 50W × 8 | " | Pseudomonas sp. P-210 ATCC 21025 | 0 | 0 | 0 |
| Diaion HPK-16 | Ascorbic acid oxidase | Cucumber | 268 | 95 | 4 |
| Diaion HPK-25 | Ascorbic acid oxidase | " | 480 | 95 | 6 |
| Diaion HPK-30 | Ascorbic acid oxidase | " | 580 | 95 | 8 |
| Diaion HPK-40 | Ascorbic acid | " | 545 | 95 | 8 |

TABLE 2-continued

| Resin | Enzyme | Enzyme-producing strain, accession number | Adsorption rate | Elution rate | Specific activity elevation*1 |
|---|---|---|---|---|---|
| Amberlite IRC-50 | Ascorbic acid oxidase | " | 47 | 95 | 3 |
| Duolite C-10 | Ascorbic acid oxidase | " | 90 | 95 | 4 |
| Diaion HPA-75 | Purine nucleoside phosphorylase | Enterobacter cloacae K4-3066 NRRL B-11155 | 25 | 85 | 4 |
| Diaion HPA-75 | Phospolipase D | Streptomyces scabies KY-667 ATCC 15485 | 17 | 40 | 20 |
| Diaion HPA-75 | Creatinine deiminase | Corynebacterium lilium KY-7742 ATCC 21644 | 4 | 95 | 10 |
| Diaion HPA-75 | Uricase | Enterobacter cloacae KY-3066 NRRL B-11155 | 30 | 90 | 4 |
| Diaion HPA-75 | Oxaloacetate decarboxylase | Pseudomonas ovalis ATCC 31171 | 100 | 55 | 2 |
| | Glucose isomerase | Streptomyces albus ATCC 21132 | 1500 | 75 | 4 |
| Diaion HPA-75 | Acetyl CoA synthetase | E. Coli ATCC 11303 | 50 | 75 | 5 |
| Diaion HPA-75 | Glycerol oxidase | Aspergillus japonicus ATCC 1042 | 150 | 33 | 3 |

*1 ratio of specific enzyme activity of the fermentation liquor before the resin treatment to that of the eluate
*2 IU: International unit It is especially noted that the ion exchange resins to be used in the present invention are superior in adsorption rate and elution rate of the enzyme to those of the macroreticular structure type which are known to be applicable for adsorption and elution of enzymes. Furthermore, the strongly acidic cation exchange resin and the strongly basic anion exchange resin can be selectively used depending upon the particular isoelectric point of the enzyme protein.

Generally, enzymes show a good stability around neutral pH, and thus operation around the neutral pH is preferable for a higher yield. Enzyme protein having an isoelectric point on the acidic side is negatively charged around the neutral pH, and thus is suitable for adsorption on a strongly basic anion exchange resin. On the other hand, enzyme protein having an isoelectric point on the alkaline side is positively charged around the neutral pH, and thus is suitable for adsorption on a strongly acidic catin exchange resin.

Enzymes to which the present invention is applicable include all species of oxidoreductases, transferases, hydrolases, lyases, isomerases, ligases and the like. Those enzymes listed in Table 2 and described in the following Examples are enumerated as particularly preferable enzymes for purification by the process of the invention.

In the present process, an enzyme in a crude enzyme solution such as a culture liquor or a cell extract solution can be adsorbed by mixing the crude enzyme solution with the ion exchange resin and stirring the mixture batchwise, or by using the ion exchange resin in a column chromatographic manner. In a batch process, the crude enzyme solution is adjusted to an appropriate pH, and the ion exchange resin is added to the crude enzyme solution in a ratio of 1/5–1/10 by volume to the solution. The mixture is gently stirred for 30–60 minutes. Though the temperature for treatment is dependent upon the stability of enzyme, a low treating temperature is generally desirable. In a column chromatographic process, the crude enzyme solution, after appropriate adjustment of pH, is passed through a resin column at the same treating temperature as in the batch process.

In either method, the adsorbed enzyme can be eluted using ordinary eluting agents such as a buffer solution, salts and detergents. Specifically, 0.1–0.5 M phosphate buffer, buffer solutions containing 0.1–1 M ammonium sulfate or 0.5% Triton X-100 are appropriate. The particular eluting agent employed must, of course, be selected depending upon the species of enzyme, amount and kind of impurities contained in the solution, the type of ion exchange resin used, etc.; but generally, a mixture of ammonium sulfate and a buffer solution is excellent for fractionating a specific enzyme with a high purity while maintaining the stability of the enzyme. Particular eluting agents can also chromatographically separate the desired enzyme from contaminating enzymes.

Characteristic advantages of use of the strongly basic anion exchange resin and strongly acidic cation exchange resin of high porous structure in enzyme purification according to the present invention are: high adsorption capacity; direct application to a crude enzyme solution containing a large amount of impurities; high fractionating capacity; the ability to chromatographically remove other contaminating enzymes, and, as a result, specific activity of the desired enzyme is greatly elevated; and the ability to utilize a high flow rate in commercial scale column chromatography.

The purified enzyme obtained according to the present process does not suffer any adverse effect upon stability in preservation and heat, even if preserved under various conditions.

Other conventional procedures for purifying an enzyme such as precipitation, dialysis, and chromatographic means can, of course, be employed in conjunction with the present process.

Certain specific embodiments of the present invention are illustrated by the following representative Examples.

EXAMPLE 1

In this example, cells obtained by centrifuging 1 l of a culture liquor of a lactate dehydrogenase-producing strain, *Lactobacillus bulgaricus* IAM 1120, are washed with 50 ml of 50 mM phosphate buffer (pH 7.0), and suspended in 250 ml of 50 mM phosphate buffer (pH 7.0). Then, glass beads (0.25–0.5 mm in diameter) are added to the suspension and the cells are disrupted in a Dyno mill.

The suspenion of disrupted cells is centrifuged to obtain 250 ml of an extract containing about 20,000 IU of lactate dehydrogenase.

The extract is then passed through a column filled with 50 ml of Diaion HPA-25 (OH type) at a flow rate of 50 ml/hr to adsorb the lactate dehydrogenase onto the ion exchange resin from the extract. The ion exchange resin is washed with 500 ml of 50 mM phosphate buffer (pH 7.0), and 200 ml of 50 mM phosphate buffer (ph 7.0) containing 0.5 M ammonium sulfate is passed through the ion exchange resin column at a flow rate of 50 ml/hr to elute the enzyme. The eluate is taken in 10 ml portions and 100 ml of fractions having a lactate dehydrogenase activity of 5 IU/ml or more is collected. The lactate dehydrogenase in the eluate has an activity of 1750 IU. The yield is 87.5% and specific enzyme activity is enhanced 15-fold.

EXAMPLE 2

In this Example, 1 l of a supernatant (filtrate of culture liquor) (lipoprotein lipase activity : 600 IU) containing lipoprotein lipase obtained by centrifuging a culture liqoor of a lipoprotein lipase-producing strain, *Rhizopus japonicus* KY 521, FERM P-3651 is passed through a column filled with 100 ml of Diaion HPA-25 (Cl form) at a flow rate of 100 ml/hr to adsorb the lipoprotein lipase onto the ion exchange resin. The ion exchange resin is washed with 1 l of 10 mM phosphate buffer (pH 6.5). Then, 300 ml of 50 mM phosphate buffer (pH 6.5) containing 1 M sodium chloride is passed through the ion exchange resin column at a flow rate of 100 ml/hr to elute the enzyme. The eluate is taken in 10 ml portions, and 180 ml of fractions having a lipoprotein lipase activity of 0.5 IU/ml or more is collected. The lipoprotein lipase in the eluate has an activity of 380 IU. The yield is 63.3% and specific enzyme activity is enhanced 11-fold.

EXAMPLE 3

In this example, cells obtained by centrifuging 5 l of a culture liquor of a glutaminase-producing strain, *Pseudomonas sp.* P-210, ATCC 21025, are washed with 2 l of 10 mM phosphate buffer (pH 6.0), and then suspended in 500 ml of 10 mM phosphate buffer (pH 6.0) containing 10 mM sodium aspartate. Then, glass beads (0.5–0.75 mm in diameter) are added to the suspension, and the cells are disrupted in a Dyno mill. The suspension of disrupted cells is centrifuged to obtain 550 ml of an extract containing about 20,000 IU of glutaminase. The extract is passed through a column filled with 250 ml of Diaion HPK-30 (Na form) at a flow rate of 250 ml/hr to adsorb the glutaminase onto the ion exchange resin. The ion exchange resin is washed with 2.5 l of 10 mM phosphate buffer (pH 6.0) containing 10 mM sodium aspartate, and then 1 l of 10 mM phosphate buffer (pH 8.0) containing 10 mM sodium aspartate and 0.5 M ammonium sulfate is passed through the ion exchange resin column at a flow rate of 250 ml/hr to elute the enzyme. The eluate is taken in 20 ml portions, and 600 ml of fractions having a glutaminase activity of 5 IU/ml or more is collected. The glutaminase in the eluate has an activity of 13,000 IU. The yield is 65% and specific enzyme activity is enhanced 42-fold.

EXAMPLE 4

In this example, cells obtained by filtration of 10 l of a culture liquor of a pyranose oxidase-producing strain, *Coriolus versicolor*, ATCC 20155, are suspended in 1 l of 50 mM tris buffer solution (pH 7.0), and glass beads (0.5–0.75 mm in diameter) are added to the suspension. The cells are then disrupted in a Dyno mill. The suspension of disrupted cells is centrifuged to obtain 800 ml of an extract containing 950 IU of pyranose oxidase. The extract is passed through a column filled with 500 ml of Diaion HPA-75 (Cl form) at a flow rate of 250 ml/hr to adsorb the pyranose oxidase onto the ion exchange resin. The ion exchange resin is washed with 2.5 l of 50 mM tris buffer (pH 7.0) containing 0.1 M ammonium sulfate, and then 2 l of 50 mM tris buffer (pH 7.0) containing 0.25 M ammonium sulfate is passed through the ion exchange resin column at a flow rate of 500 ml/hr to elute the enzyme. The eluate is taken in 20 ml portions, and 750 ml of fractions having a pyranose oxidase activity of 0.25 IU/ml or more is collected. The pyranose oxidase in the eluate has an activity of 732 IU. The yield is 77% and specific enzyme activity is enhanced 17.8-fold.

EXAMPLE 5

In this Example, 1 l of a supernatant (filtrate of culture liquor) containing protease (protease activity : 600 KIU) obtained by centrifuging a culture liquor of a protease-producing strain, *Serratia sp.*, ATCC 21074, is passed through a column filled with 50 ml of Diaion HPA-75 (Cl form) at a flow rate of 200 ml/hr to adsorb the protease onto the ion exchange resin. The ion exchange resin is washed with 150 ml of 10 mM phosphate buffer (pH 7), and then 150 ml of 10 mM phosphate buffer (pH 7) containing 1 M ammonium sulfate is passed through the ion exchange resin column at a flow rate of 50 ml/hr to elute the enzyme. The eluate is taken in 10 ml portions, and 80 ml of fractions having a protease activity of 2,000 IU/ml or more is collected. The protease in the eluate has an activity of 510 KIU. The yield is 85% and specific enzyme activity is enhanced 8-fold.

What is claimed is:

1. A process for purifying an enzyme in a solution containing the enzyme which comprises bringing said solution into contact with a strongly acidic cation exchange resin of high porous type selected from the group consisting of Diaion HPA-25 and HPA-75, or a strongly basic anion exchange resin of high porous type wherein a quaternary ammonium group is introduced as exchange groups into a styrene-divinyl benzene polymer matrix of macro-reticular structure to adsorb the enzyme thereon, passing an eluting agent through said ion exchange resin to elute said enzyme therefrom and recovering active fractions of the eluate to obtain a purified enzyme solution.

2. A process according to claim 1 wherein said strongly basic anion exchange resin of high porous type is Diaion HPK-16, HPK-25, HPK-30 or HPK-40.

3. A process according to claim 1 wherein said enzyme is oxidoreductase, transferase, hydrolase, lyase, isomerase or ligase.

4. A process according to claim 1 wherein said resin is characterized by an average pore radius of at least 150 Å, a surface area of at least 5 m$^2$/g dry resin, and a pore volume of at least 0.2 cm$^3$/g dry resin.

5. A process according to claim 1 wherein said adsorption step is carried out at about neutral pH.

* * * * *